US006616598B2

(12) United States Patent
Kaushansky et al.

(10) Patent No.: US 6,616,598 B2
(45) Date of Patent: Sep. 9, 2003

(54) DOCKING STATION FOR A TRANSPORTABLE DEVICE

(75) Inventors: Yefim Kaushansky, Fairlawn, NJ (US); Edmund G. Pacenka, Westwood, NJ (US)

(73) Assignee: Datascope Investment Corp., Montvale, NJ (US)

( * ) Notice: Subject to any disclaimer, the term of this patent is extended or adjusted under 35 U.S.C. 154(b) by 0 days.

(21) Appl. No.: 09/955,349

(22) Filed: Sep. 18, 2001

(65) Prior Publication Data

US 2003/0055309 A1 Mar. 20, 2003

(51) Int. Cl.[7] .................................................. A61M 1/10
(52) U.S. Cl. ........................................... 600/18; 600/16
(58) Field of Search ...................................... 600/16, 18

(56) References Cited

U.S. PATENT DOCUMENTS 6,346,139 B1 * 2/2002 Czabala ....................... 95/130
6,364,331 B1 * 4/2002 Yap ........................ 280/47.371

OTHER PUBLICATIONS

"Use of the Transport Docking Station and Mobilizer", Datascope System 97 Intra–Aortic Balloon Pump Operating Instructions, Chapter 5, Section 5.5, added to instructions on Jun. 28, 1995.
"Clinical Environments", Arrow ACAT(TM) 1 Intra–Aortic Balloon Pump (IABP) System Operating Manuel, Chapter 5, Section 5.2, Part Number: IAM–9001, Revision 2.

* cited by examiner

Primary Examiner—Carl Layno
(74) Attorney, Agent, or Firm—J. Gary Mohr

(57) ABSTRACT

A mounting device for securing transport patient connected equipment, specifically an intra-aortic balloon pump (IABP), in the typically crowded medical transport vehicle. An engagement stud on the IABP slides into a spring-loaded latch connected to a vehicle mounted base. The engagement stud configuration allows the user to engage the IABP from any desired direction, i.e. slide the pump from any of the four sides onto the mount. No effort is required from the user beyond the pushing motion for locking the IABP onto the mount.

17 Claims, 10 Drawing Sheets

DOCKING STATION FOR A TRANSPORTABLE DEVICE

BACKGROUND OF THE INVENTION

1. Field of the Invention

The invention relates to a docking station. More particularly, the invention relates to a mounting device for securely docking a piece of equipment, such as an intra-aortic balloon pump (IABP).

2. Description of the Prior Art

An intra-aortic balloon pump (IABP) is utilized to provide mechanical assistance to the failing heart. Often, IABP therapy must be sustained as patients are transported from one medical facility to another. In these cases, transport may be accomplished via ambulance, helicopter or airplane. Typically, IABP systems have the form factor similar to a two drawer file cabinet, and weigh in the range of 75 to 200 lbs.

For safety during transport, it is essential to secure the patient and IABP from movement. This need is particularly acute in aircraft, where three dimensional movements are possible and space is limited. Because the patients are generally acutely ill, it is important to minimize the time associated with transport. For this reason, the IABP and patient must be secured and released rapidly from the transport vehicle.

Typically transport vehicles have limited size and floor space. The floor plans of vehicles are highly variable. In all cases, it is desirable secure the IABP in a specific orientation with respect to the patient.

The selected orientation takes into consideration:
(a) the need for access to the patient by attending clinical staff; (b) the need for access to the IABP's controls by attending clinical staff; (c) the need of attending clinical staff to view the IABP's visual displays; and (d) the routing of essential electrical and pneumatic interconnections between the patient and the IABP.

Currently commercially available equipment restraining devices are mechanically complex and require a relatively large number of specially designed and manufactured parts. Furthermore, mounting the IABP requires a significant amount of effort. The complexity and ergonomical "unfriendliness" becomes clear when looking at, for example, Arrow International's 1998 Operation Manual which details the mounting of Arrows' pump to the transport vehicle. According to the manual, one has to reach under the center left of a lock down bracket on the IABP and pull down a locking pin. Next, one has to rotate the pin a quarter turn to retain it in an unlocked position. After which one has to roll the IABP onto a bracket having a railing and then reach under the IABP again to turn the pin into a locked position.

Another disadvantage of the Arrow pump mounting device is that it is direction specific. One has to roll the pump sideways for mounting because the mount does not accept any other approach position. As indicated above, this limitation can be frustrating and cost precious time in emergency situations.

While the present intra-aortic balloon pump mounting systems may be suitable for the particular purpose employed, or for general use, it is not as suitable for the purposes of the present invention as disclosed hereafter.

SUMMARY OF THE INVENTION

Accordingly, it is an object of the invention to produce an IABP mounting device which constrains motion in all three axes.

It is another object of the invention to produce an IABP mounting device which rapidly secures and releases the IABP.

It is yet another object of the invention to produce an IABP mounting device which allows the IABP to be secured from any orientation.

It is still another object of the invention to produce an IABP having a small "footprint", i.e. requiring minimum additional floor space within a transport vehicle.

The invention is a mounting device for securing for transport patient connected equipment, specifically an IABP, in the typically crowded medical transport vehicle. An engagement stud on the IABP slides into a spring-loaded latch connected to a vehicle mounted base. The engagement stud configuration allows the user to engage the IABP from any desired direction (i.e. slide the pump from any of the four sides onto the mount). No effort is required from the user beyond the pushing motion for locking the IABP onto the mount.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
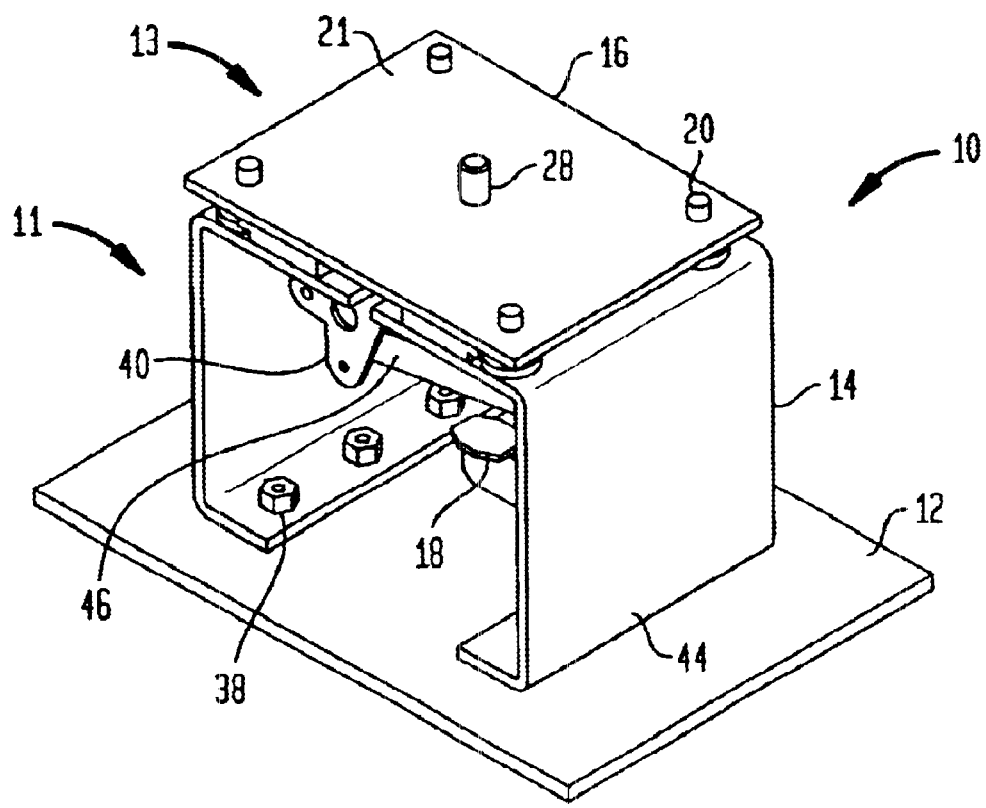
FIG. 1 is a perspective view of the transport mount system of the present invention.

FIG. 1 illustrates a perspective view of transport mount system 10 of the present invention comprising a docking station portion 11 and a transportable device portion 13. Docking station portion 11 comprises a vehicle interface or mounting plate 12, housing 14, latch 40, and release lever 18. Transportable device portion 13 comprises an adapter plate 16 which is connected to the underside of an intra-aortic balloon pump 22 (see FIG. 3) by means of four engagement studs 20, best seen in FIG. 2, and a latching post 28 which project from both an upper surface 21 and a lower surface 24 of the engagement plate 16.

Figure 2:
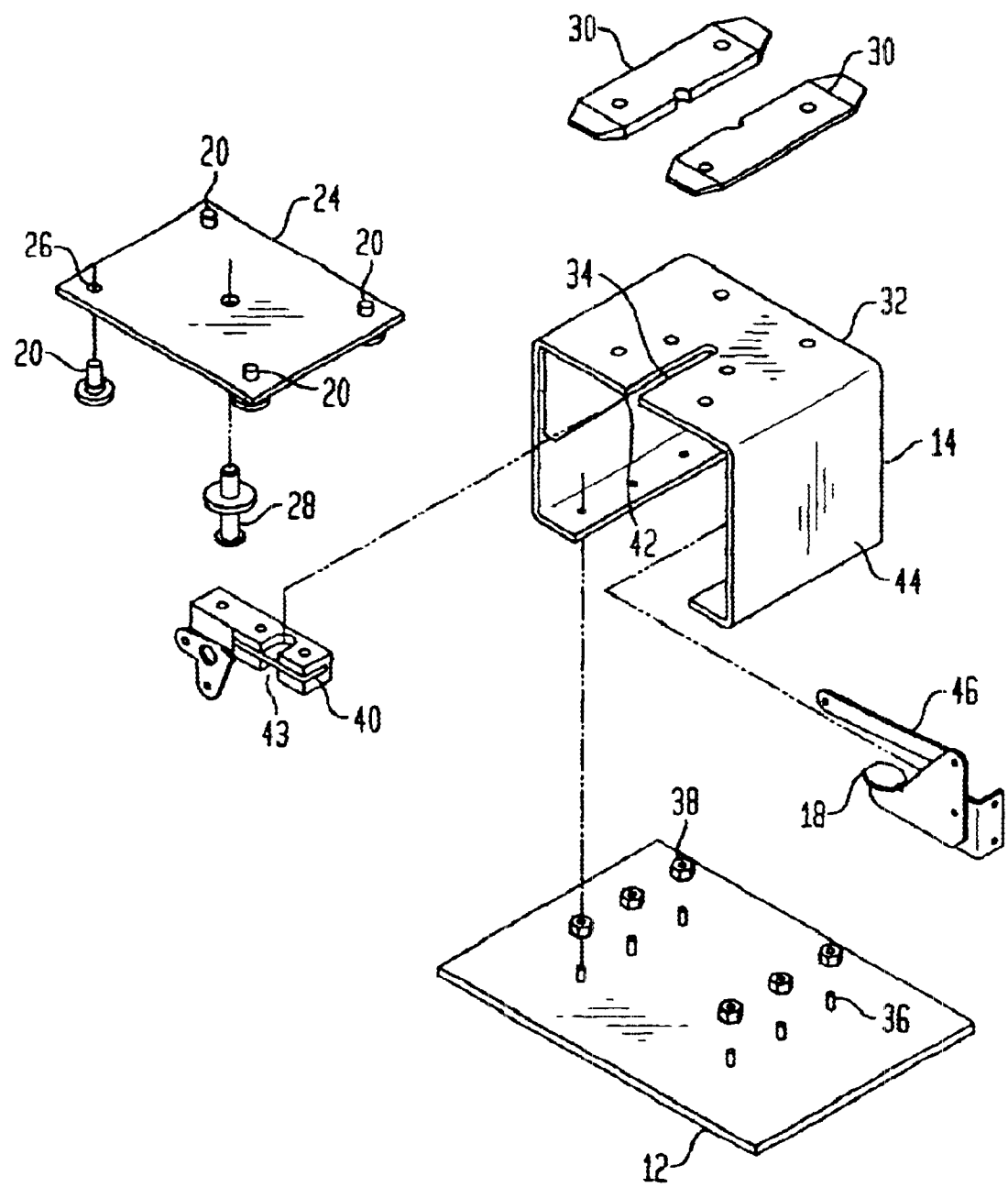
FIG. 2 is an exploded view of the transport mount system.
Figure 3:
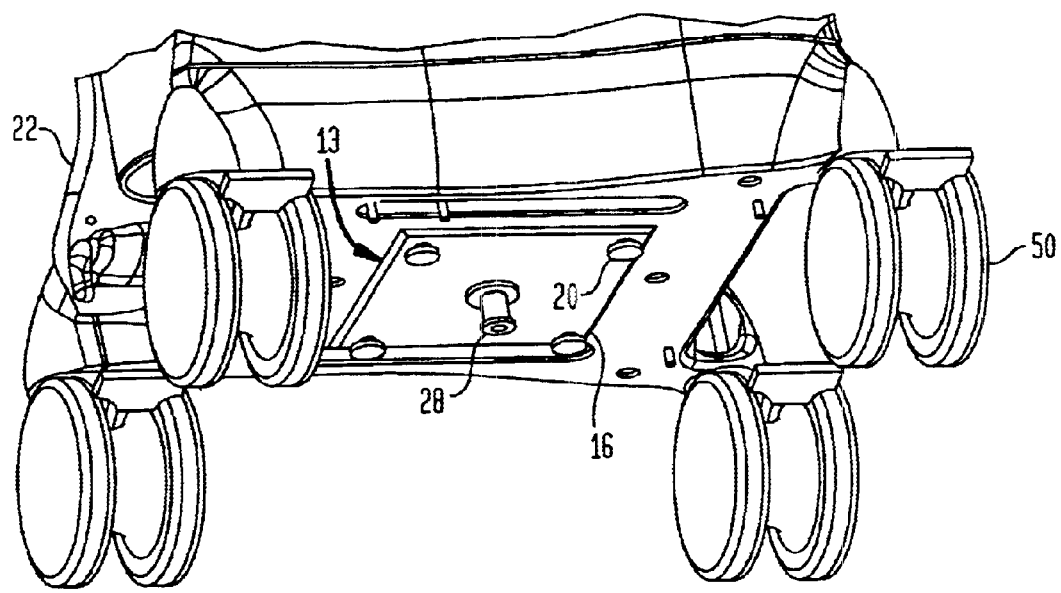
FIG. 3 is a perspective view of the underside of an intra-aortic balloon pump (IABP).

FIG. 2 is an exploded view of the transport mount system 10 of FIG. 1. Engagement studs 20 and latching post 28 pass through holes 26 in engagement plate 16 and screw into an underside of IABP 22, as can be seen in FIG. 3. FIG. 3 is a perspective view of a bottom portion of IABP 22. Alternatively, engagement studs 20 and/or latching post 28 may simply project from lower surface and an alternate means, such as an adhesive or screws, may be used to secure engagement plate 16 to IABP 22. Furthermore, engagement plate 16 may be eliminated and engagement studs 20 and/or latching post 28 may be incorporated directly into IABP 22.

A track bar 30, consisting of two mirror halves, is connected to a top outer surface 32 of housing 14. Housing 14 has a latching post slot 34. Housing 14 is connected to mounting plate 12 by means of bolts 36 extending through mounting plate 12 and fastened to nuts 38. Note that any other known fastening means, such as but not limited to welding, may be used as well. Latch 40 is connected to a top lower surface 42 of housing 14 such that latch slot 43 lines up with latching post slot 34. Release lever 18 is supported by a side wall 44 of housing 14 and is connected via linkage 46 to latch 40.

Note that latch 40 as illustrated is a standard vehicle slam latch that meets Federal Motor Vehicle Safety Standard #206. Alternatively, latch 40 may be a slam-capable latch, typically used in industrial cabinetry applications, or any type of post securing means known in the art. For example, a spring detente system may be used to secure latching post 20. Alternatively, latch 40 may be of the flash mountable or paddle/handle operated latches types as disclosed in U.S. Pat. Nos. 4,320,642, 4,917,412, 4,896,906, and 5,069,491, all herein incorporated by reference in their entirety.

Figure 4:
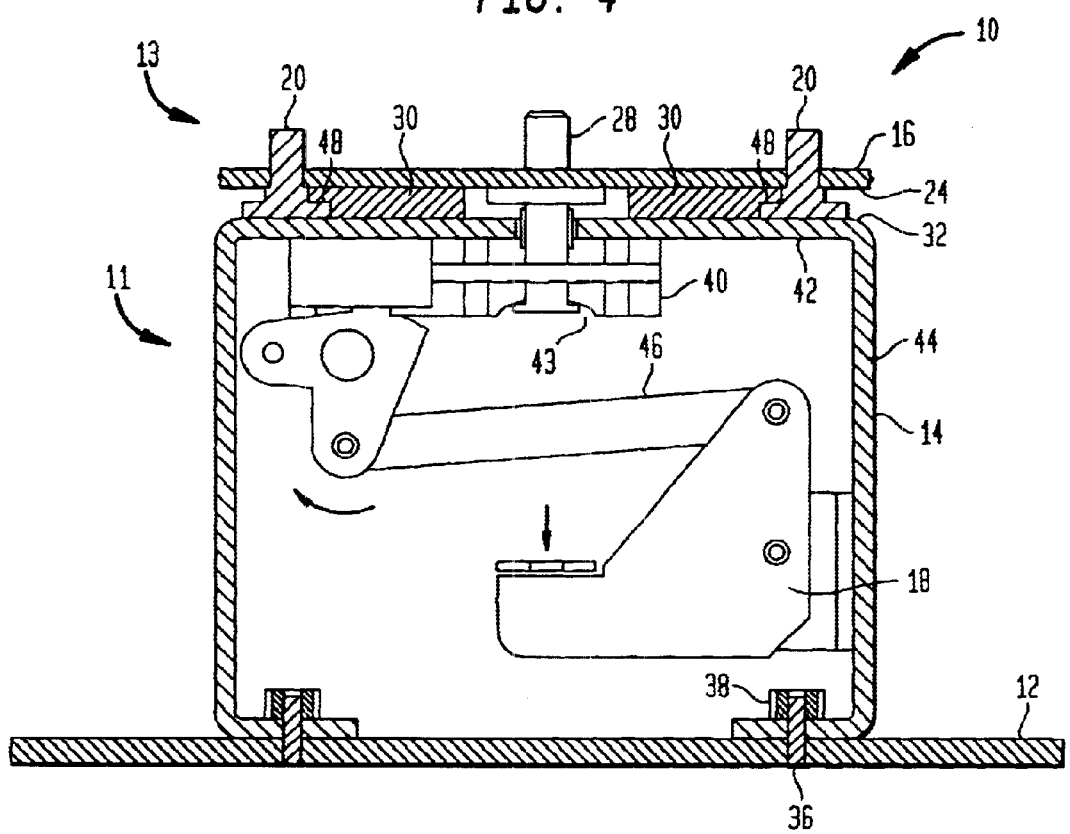
FIG. 4 is a side view of the transport mount system.

FIG. 4 illustrates a side view of transport mount system 10 and more clearly shows the means for engaging and releasing guide latching post 28. Note that track bar 30 together with top upper surface 32 of housing 14 create a pair of grooves 48 in which engagement studs 20 travel as they guide latching post 28 to latch 40. Engagement studs 20 also help stabilize the IABP 22 and secure the IABP 22 to housing 14.

Figure 5:
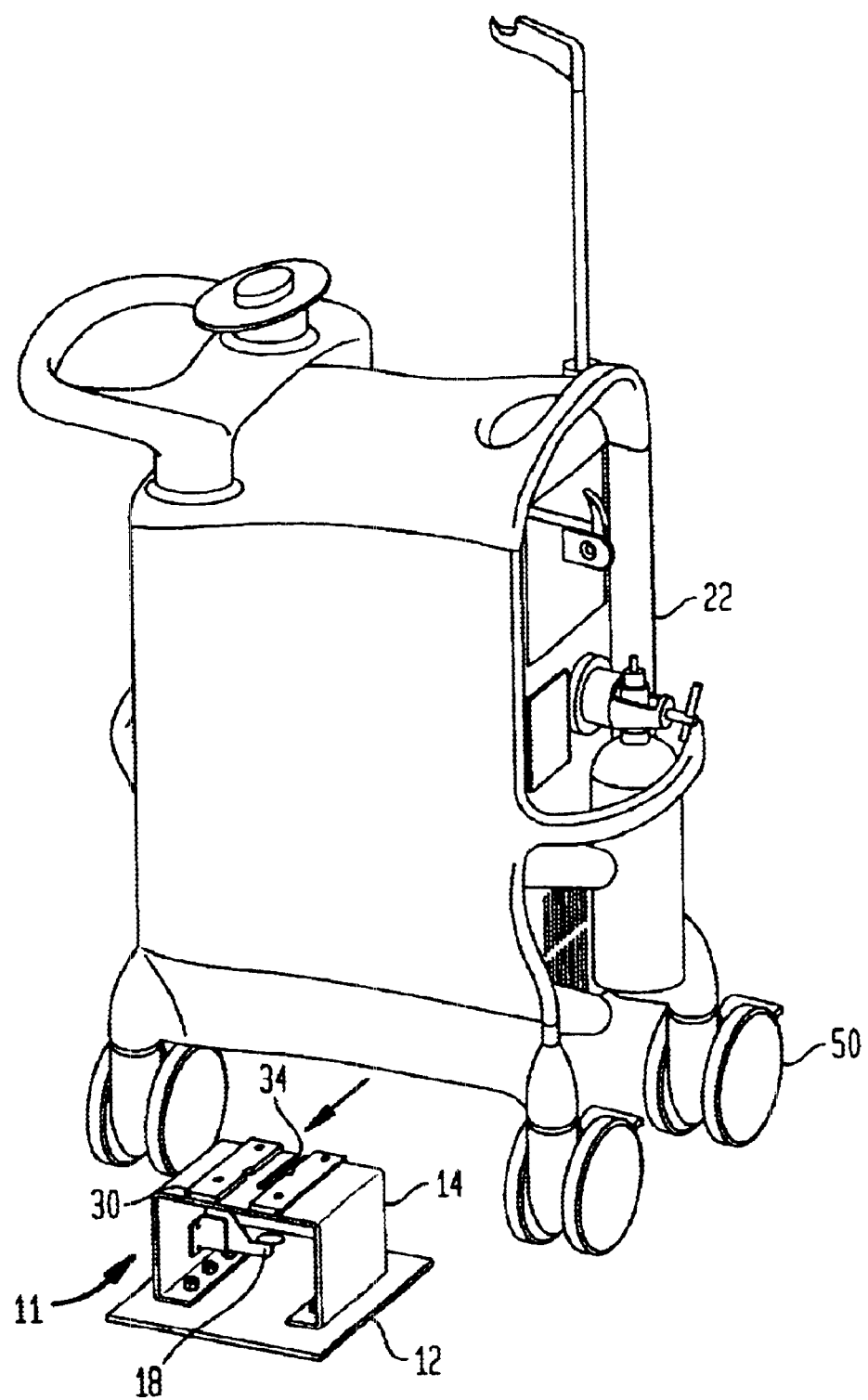
FIG. 5 is a perspective view of the IABP and the mount system.
Figure 6:
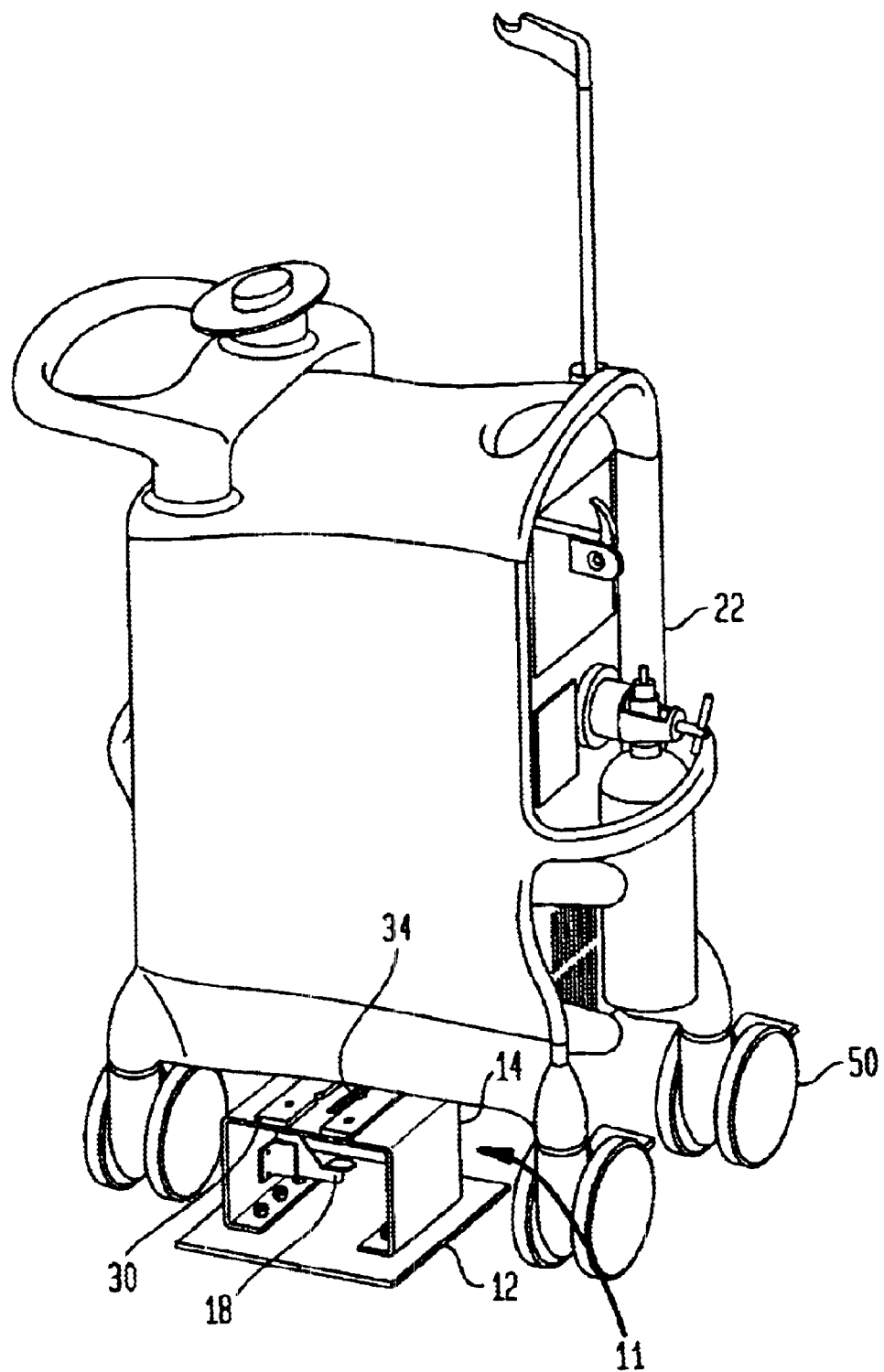
FIG. 6 is perspective view of the IABP, being mounted from the side, partially over but not engaged to the mount system.
Figure 7:
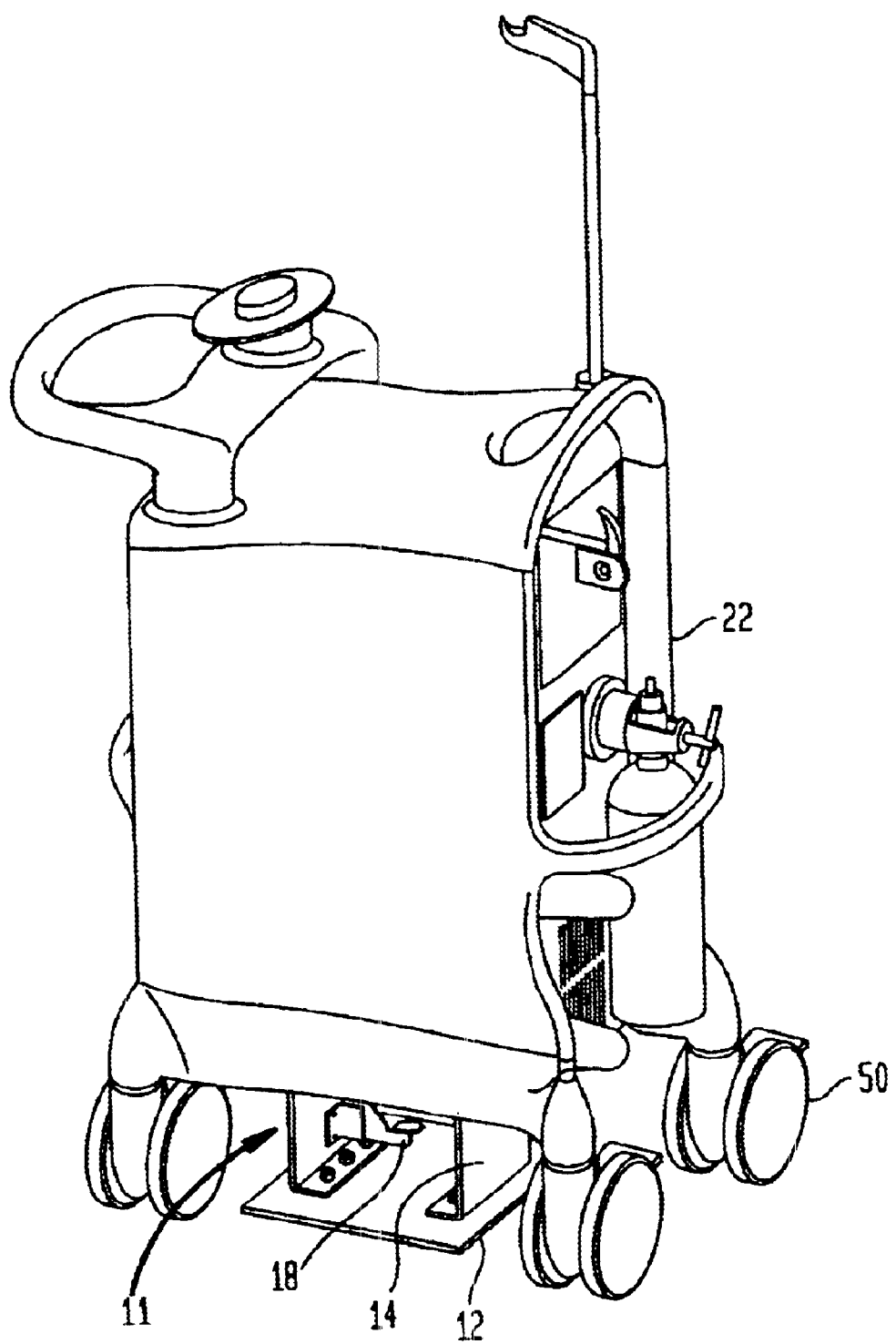
FIG. 7 is a perspective view of the IABP, mounted from the side, over and secured to the docking station portion of the mount system.
Figure 8:
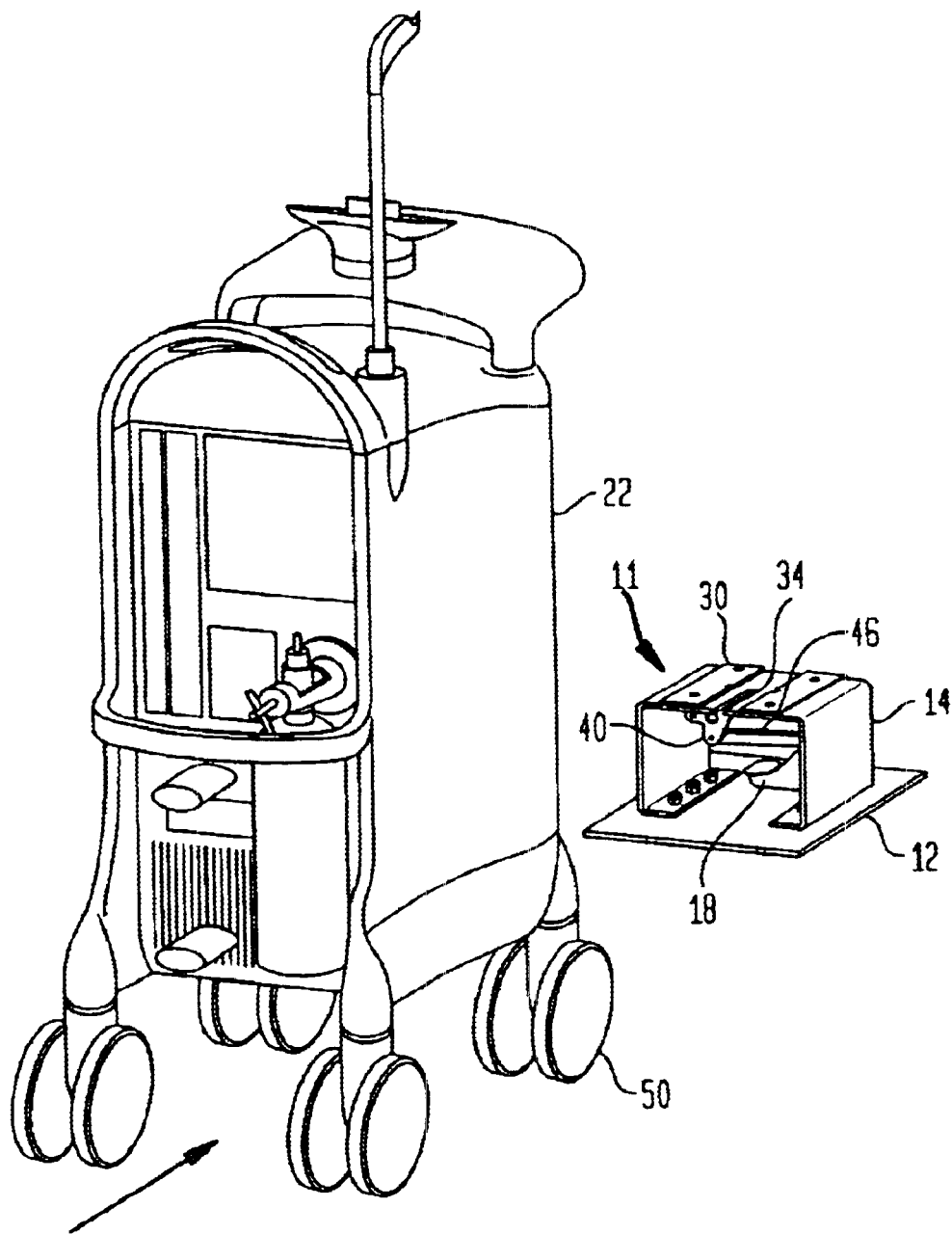
FIG. 8 is a perspective view of the IABP and the mount system.
Figure 9:
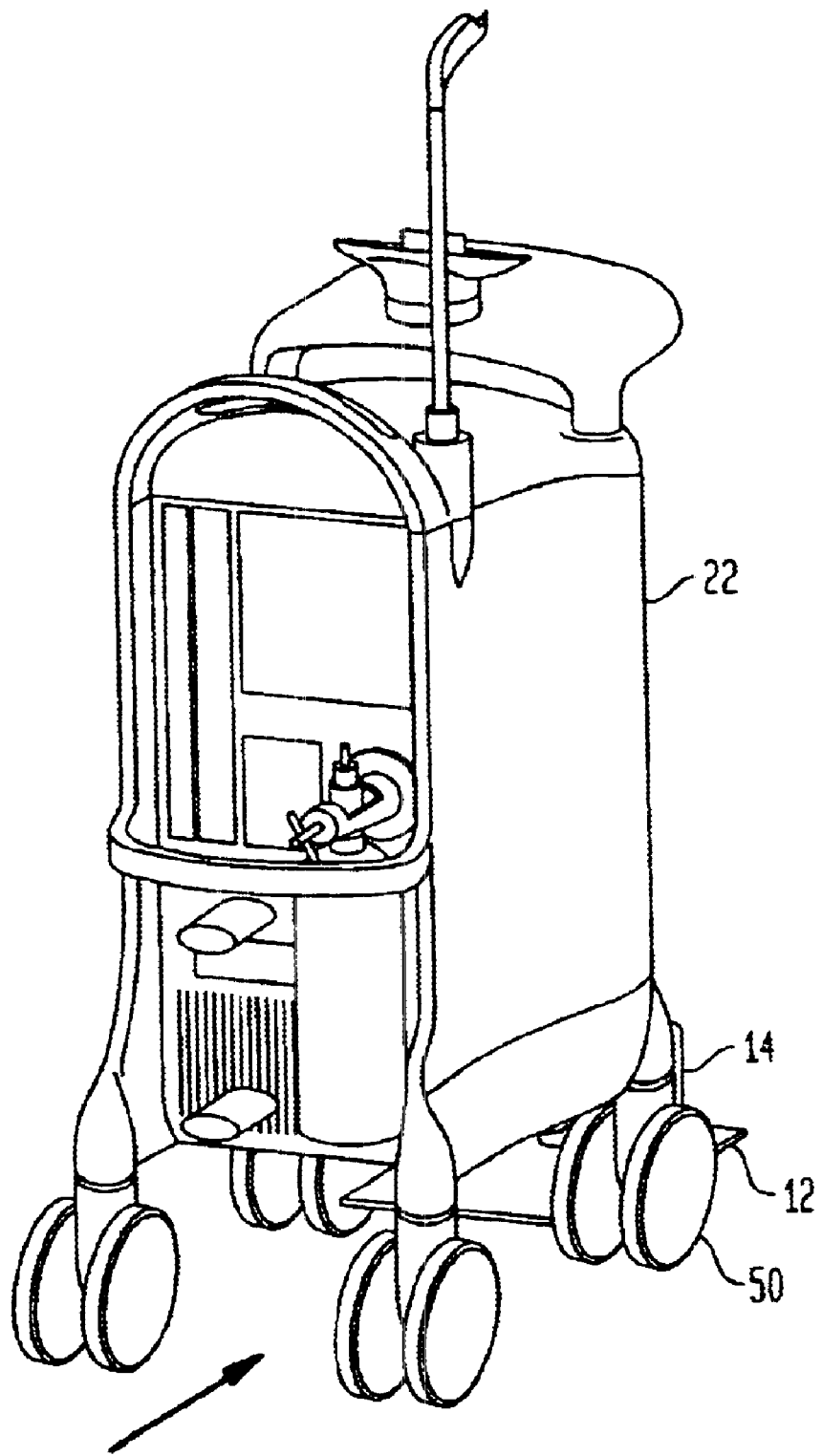
FIG. 9 is perspective view of the IABP, being mounted from the front, partially over but not engaged to the mount system.
Figure 10:
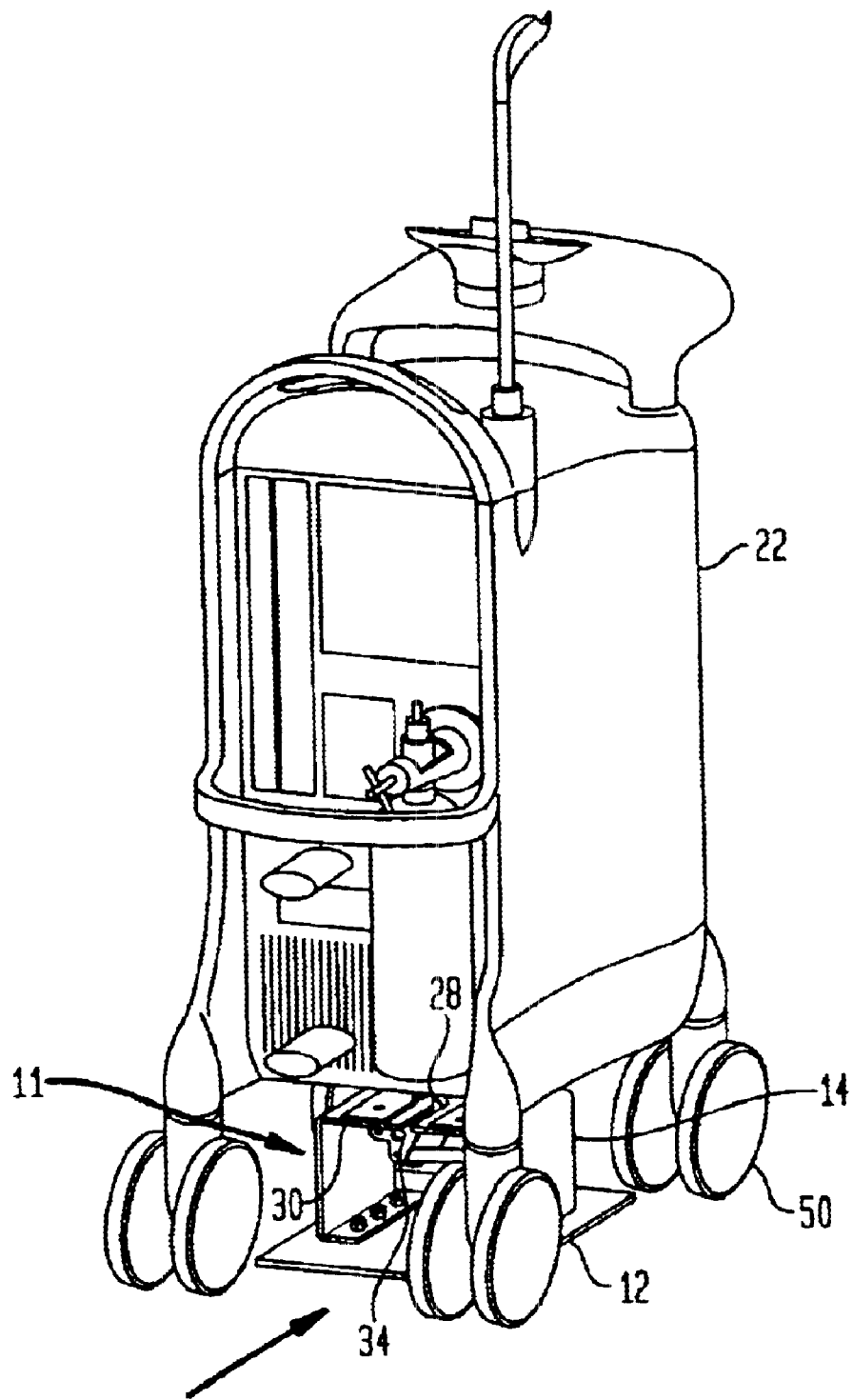
FIG. 10 is a perspective view of the IABP, mounted from the front, over and secured to the docking station portion of the mount system.

Guide latching post 28 is shown in a latched or engaged position. This state of affairs is accomplished by rolling IABP 22, as illustrated in FIGS. 5–7 or in FIGS. 8–10, on wheels 50 in the direction of the arrow towards mounting plate 12 such that engagement studs ride in grooves 48 and guide latching post 28 travels in latching post slot 34 until latch 40 engages and secures latching post 28. In order to release the IABP 22 from latch 40 one activates release lever 18 by pressing down on it and then pulls IABP 22 away from housing 14. Note that release lever 18 may alternatively be designed such that an alternate directional force, such as an upward or sideways force, releases latching post 28. FIGS. 5–7 illustrate IABP 22 being mounted from the side and FIGS. 8–10 illustrate IABP 22 being mounted from the front. The latching post configuration allows the user to engage IABP 22 from any desired direction (i.e. slide IABP 22 from any of the four sides onto transport mount system 10). Note that any pump locomotion means known in the art other than the four wheels as illustrated may be used. Furthermore, a set of two or three wheels with a balancing support may also be used. Regardless of the number of wheels used frame 14 will fit between any pair of adjacent wheels.

As many apparently widely different embodiments of the present invention can be made without departing from the spirit and scope thereof, it is to be understood that the invention is not limited to the specific embodiments thereof except as defined in the appended claims.

What is claimed is:

1. A docking station for a transportable device, said docking station comprising a docking station portion and a transportable device portion, said transportable device portion comprising a latching post connected to the transportable device, said docking station portion comprising a frame and a securing means, said frame connected to and supporting the securing means such that the latching post traveling over the frame is engageable by the securing means.

2. The docking station as claimed in claim 1 wherein said frame has a frame slot and is connected to the securing means such that the post on the transportable device portion traveling through said slot engages the securing means.

3. The docking station as claimed in claims 1 or 2 wherein the docking station further comprises one or more grooves and wherein the transportable device portion further comprises two or more guide posts which are slidable within the grooves, as the transportable device is moved over the frame and the guide posts slide within the grooves the transportable device is guided to a position where the transportable device portion is engaged by the securing means.

4. The docking station as claimed in claims 1 or 2 wherein the transportable device comprises an intra-aortic balloon pump and wherein the latching post projects from a lower surface of the intra-aortic balloon pump.

5. The docking station as claimed in claims 1 or 2 wherein the transportable device portion is supported by two or more wheels, the frame fits between any two adjacent wheels.

6. The docking station as claimed in claims 1 or 2 wherein the transportable device comprises an intra-aortic balloon pump supported by two or more wheels and wherein the latching post projects from a lower surface of the intra-aortic balloon pump, the frame fits between any two adjacent wheels.

7. The docking station as claimed in claim 1 wherein the engagement means comprises a latch.

8. The docking station as claimed in claim 1 wherein the engagement means comprises a standard automobile door latch.

9. The docking station as claimed in claim 1 wherein the engagement means comprises a spring detente system.

10. The docking station as claimed in claim 1 wherein the transportable device portion comprises a plate having an upper surface and a lower surface, the upper surface of the plate is connected to and contacts the transportable device, the latching post projects from a lower surface of the plate.

11. The docking station as claimed in claims 1 or 2 wherein the transportable device comprises an intra-aortic balloon pump supported by three or more wheels and wherein the latching post projects from a lower surface of the intra-aortic balloon pump, the frame fits between any two adjacent wheels.

12. A method for securing a transportable device to a docking station, said docking station comprising a docking station portion and a transportable device portion, said transportable device portion comprising a latching post connected to the transportable device, said docking station portion comprising a frame and a securing means connected to said frame, the method comprising the step of moving the transportable device such that the latching post engages the securing means.

13. The method as claimed in claim 12 wherein the frame has a frame slot and wherein the transportable device is moved such that the latching post travels in the slot, the slot guides the latching post to the engagement means.

14. The method as claimed in claims 12 or 13 wherein the docking station further comprises one or more grooves and wherein the transportable device portion further comprises two or more guide posts which are slidable within the grooves, and further comprising the preliminary step of sliding the guide posts into their respective grooves, as the guide posts slide within the grooves the transportable device is guided to a position where the latching post is engaged by the securing means.

15. The method as claimed in claims 12 or 13 wherein the docking station further comprises one or more grooves, the transportable device portion further comprises two or more guide posts which are slidable within the grooves, the transportable device comprises an intra-aortic balloon pump and the latching post projects from a lower surface of the intra-aortic balloon pump, and further comprising the preliminary step of sliding the guide posts into their respective grooves, as the guide posts slide within the grooves the transportable device is guided to a position where the latching post is engaged by the securing means.

16. The method as claimed in claim 12 wherein the transportable device is supported by three or more wheels and wherein the transportable device is rolled over the docking station portion to engage the latching post to the engagement means, the frame fitting between any pair of adjacent wheels.

17. The method as claimed in claim 12 wherein engagement means comprises a latch, wherein the transportable device is supported by three or more wheels, and wherein the transportable device is rolled over the docking station portion to engage the latching post to the latch, the frame fitting between any pair of adjacent wheels.

* * * * *